United States Patent [19]
Baker

[11] Patent Number: 5,749,831
[45] Date of Patent: May 12, 1998

[54] FETAL CARDIAC MONITORING UTILIZING UMBILICAL BLOOD FLOW PARAMETERS AND HEARTBEAT INFORMATION

[76] Inventor: Donald A. Baker, P.O. Box 742, Deer Park, Wash. 99006-0742

[21] Appl. No.: 880,352

[22] Filed: Jun. 23, 1997

[51] Int. Cl.$^6$ .................................................. A61B 5/026
[52] U.S. Cl. .......................... 600/301; 600/483; 600/504; 600/438; 600/455; 600/454
[58] Field of Search ..................................... 600/301, 304, 600/407, 437, 438, 453, 454, 483, 504, 455, 511, 528, 364

[56] References Cited

U.S. PATENT DOCUMENTS

| | | |
|---|---|---|
| 3,561,430 | 2/1971 | Filler et al. |
| 3,581,735 | 6/1971 | Gentner et al. |
| 3,599,628 | 8/1971 | Abbenante .............................. 600/511 |
| 3,780,726 | 12/1973 | Hatke . |
| 4,086,917 | 5/1978 | Burks et al. |
| 4,211,237 | 7/1980 | Nagel . |
| 4,299,234 | 11/1981 | Epstein et al. |
| 4,357,944 | 11/1982 | Mauser et al. |
| 4,367,752 | 1/1983 | Jimenez et al. |
| 4,492,120 | 1/1985 | Lewis et al. |
| 4,757,823 | 7/1988 | Hofmeister et al. |
| 4,781,200 | 11/1988 | Baker . |
| 4,869,260 | 9/1989 | Young et al. |
| 4,915,115 | 4/1990 | Sasaki et al. |
| 5,257,627 | 11/1993 | Rapoport . |
| 5,265,613 | 11/1993 | Feldman et al. |
| 5,360,005 | 11/1994 | Wilk . |
| 5,383,463 | 1/1995 | Friedman .............................. 600/455 |
| 5,419,332 | 5/1995 | Sabbah et al. |

FOREIGN PATENT DOCUMENTS

| | | |
|---|---|---|
| WO 80/00054 | 1/1980 | European Pat. Off. |
| 56-29971 | 3/1981 | Japan . |
| 1348154 | 3/1974 | United Kingdom . |
| 2121967 | 1/1984 | United Kingdom . |

OTHER PUBLICATIONS

Schmidt, Klaus G., M.D., et al.; *Assessment of Right Ventricular Performance by Doppler Echocardiography in Patients After Intraatrial Repair of Aortopulmonary Transposition in Infancy or Childhood;* American College of Cardiology, 1989, pp. 1578–1585.

Seward Medical Systems Limited brochure; *Fetatrack DD250; Fetatrack 210; Fetatrack 260;* 8 pages.

Giles, Warwick B., et al.; *The effect of epidural anaesthesia for caesarean section on maternal uterine and fetal umbilical artery blood flow velocity waveforms;* British Journal of Obstetrics and Gynaecology, Jan. 1987; vol. 94, pp. 55–59.

Thompson, Rosemary S., et al.; *Doppler Waveform Pulsatility Index and Resistance, Pressure and Flow in the Umbilical Placental Circulation: An Investigation Using a Mathematical Model;* Ultrasound in Medicine and Biology, vol. 16, No. 5, pp. 449–458.

Wells, P. N. T.; *Biomedical Ultrasonics;* Academic Press, 1977; pp. 392–397.

(List continued on next page.)

*Primary Examiner*—William E. Kamm
*Assistant Examiner*—Kennedy J. Schaetzle
*Attorney, Agent, or Firm*—Wells, St. John, Roberts, Gregory & Matkin, P.S.

[57] ABSTRACT

Methods and systems for monitoring to assess the health of a fetus being carried within a mother. The methods include sensing fetal heart information using a fetal heart sensor; determining at least one fetal heart rate measure from the fetal heart rate information; detecting umbilical flow information relating to the flow of blood within the umbilical; deriving at least one umbilical flow indicator from at least the umbilical flow information; and analyzing the fetal heartbeat measure and umbilical flow measure to produce at least one fetal health parameter. The systems include the heartbeat sensor, umbilical flow detector, and a processor which allows analysis of the information obtained from the sensor and detector to provide an indication of fetal health.

36 Claims, 6 Drawing Sheets

OTHER PUBLICATIONS

Lewinsky, Reuven M.; *Cardiac systolic time intervals and other parameters of myocardial contractility as indices of fetal acid–base status*; Bailliere's Clinical Obstetrics and Gynaecology, 1994, pp. 663–681.

Ando, Hiromi, M.D., et al.; *New technique for analysis of cardiac energetics using a modified Fenn equation*; The Journal of Thoracic and Cardiovascular Surgery, 1989; pp. 565–574.

G. Alec Rooke et al.; "Work as a Correlate of Canine Left Ventricular Oxygen Consumption, and the Problem of Catecholamine Oxygen Wasting"; Circulation Research, vol. 50, No. 2, Feb. 1982; pp. 273–286.

Edmund H. Sonnenblick et al.; "Velocity of contraction as a determinant of myocardial oxygen consumption"; Cardiology Branch, National Heart Institute, National Institutes of Health, Bethesda, Maryland; pp. 919–927.

FETAL CARDIAC MONITORING UTILIZING UMBILICAL BLOOD FLOW PARAMETERS AND HEARTBEAT INFORMATION

TECHNICAL FIELD

This invention relates to methods and systems for monitoring a pregnant mother to assess the health of a fetus being carried within the mother by considering the flow of blood within the umbilical cord.

BACKGROUND OF THE INVENTION

The medical profession has long endured great difficulties in attempting to monitor fetal health and well-being. The position of the fetus within the womb, surrounded by the placenta, amnion and amniotic fluid makes direct examination of the fetus extremely difficult. Direct examination also is potentially injurious to the fetus or expectant mother and in many cases such examination is simply not possible as a practical matter.

Traditional methods for investigating the condition of a fetus have included using a stethoscope to listen to the fetal heartbeat. Also common are associated physical examination by palpitation of the pregnant mother. The pregnant mother is sometimes referred to in the medical profession as a gravida.

Although these common techniques are useful, they are limited in the amount of information which can be derived. Such traditional techniques do not provide a sufficient amount of information concerning the health of the fetus to diagnose a number of fetal health problems. Further, such techniques do not indicate fetal response to varying environmental conditions and unexpected occurrences confronting the gravida and fetus.

Other prior techniques for determining fetal health problems and various conditions have included the use of ultrasound. Ultrasound techniques generally use an apparatus which includes an ultrasonic transducer which generates ultrasonic vibrations which are directed at the fetal heart or other fetal organs. In many ultrasound systems ultrasonic waves are generated and directed at the fetus and reflect off the fetus. The reflected ultrasound waves are then sensed by an appropriate sensor and processed. In one type of ultrasound, called Doppler ultrasound, the systems determine the frequency shift associated with the reflection from the moving fetal heart valve according to well-known Doppler effect principles. The information gained by such technique is then analyzed and integrated to provide information about the fetus, including the fetal heart rate.

Prior art techniques employing ultrasound for fetal analysis have been relatively difficult and imprecise due to difficulties in obtaining data about the fetus. The fetus frequently moves within the womb during such attempts to examine using ultrasound. Although this is not a problem in ultrasound imaging which shows the fetal movement, it is a significant problem in gaining information about fetal health other than movement. Since movement is a relatively crude analysis by itself, great difficulties remain in obtaining reliable fetal health monitoring information.

Also known are techniques using ultrasound for the determination of umbilical blood flow. These techniques look at the velocity of blood during systole and a baseline velocity of the blood during diastole in order to derive a ratio therebetween. This ratio is typically called the A/B ratio and is of only limited value in assessing the health of the fetus. Prior studies have merely indicated that the A/B ratio is a measure of the fluid resistance offered in the fetal and placental fluid systems. This provides only very limited information of direct fetal cardiac health, and is only of utility in severe cases of fetal health malfunction. Such an analysis has not been useful as an indicator of more general fetal health having sensitivity to a variety of fetal health concerns.

Other techniques for determining fetal health exist, but are limited in scope. For example, a so-called non-stress test assesses the health of a fetus based on fetal heart rate, fetal movement, and uterine activity. By noting accelerations of fetal heart rate along with fetal movement, an assessment is made as to the health of the fetus. The assessment is based upon recognizing activity of the fetus which should cause increased fetal heart rate. However, the non-stress test is unable to assess more specific fetal cardiac problems and performance. The non-stress test is also not effective in many or most situations to provide an indication of more general fetal health problems or fetal metabolic processes, such as cardiac oxygen consumption, cardiac efficiency, and myocardial contractility.

Thus there is a strong and long-felt need in the art of fetal health monitoring for systems and methods which provide improved indications of fetal cardiac condition and more general fetal health.

BRIEF DESCRIPTION OF THE DRAWINGS

Preferred embodiments of the invention are described below with reference to the accompanying drawings, which are briefly described below.

DETAILED DESCRIPTION OF THE PREFERRED EMBODIMENTS

Figure 1:
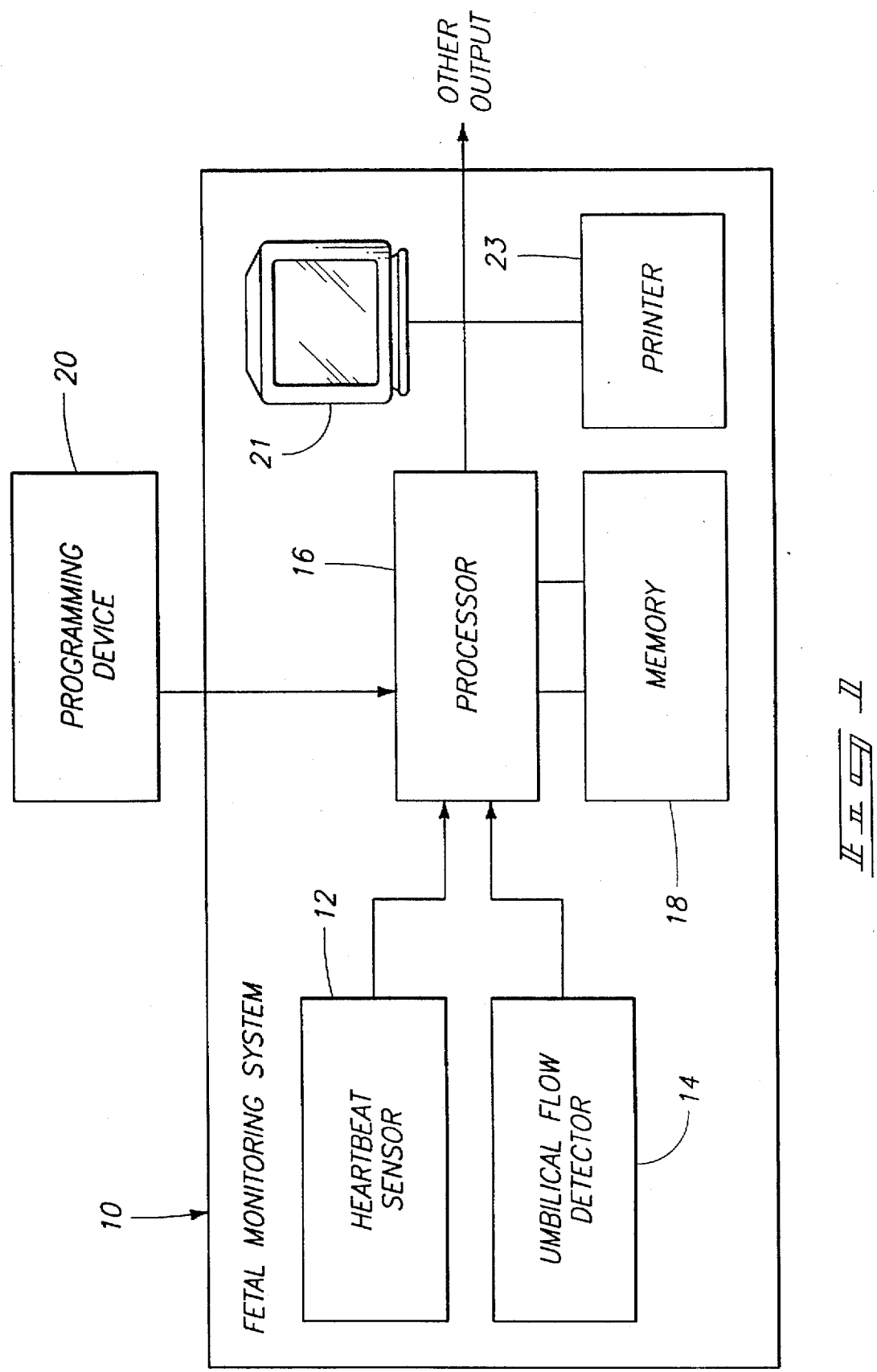
FIG. 1 is a block diagram of a preferred fetal monitoring system according to the present invention.

This disclosure of the invention is submitted in furtherance of the objectives of patent laws to promote the progress of science, technology and the useful arts.

TABLE 1

| Listing of Subsections of Detailed Description and Pertinent Items with Reference Numerals and Page Numbers | |
|---|---|
| First Preferred System | 6 |
| fetal monitoring system 10 | 6 |
| heartbeat sensor 12 | 6 |
| umbilical flow detector 14 | 6 |
| processor 16 | 6 |
| memory 18 | 7 |
| Heartbeat Sensor | 7 |
| fetal heartbeat sensor 12 | 7 |
| period of systole 110 | 9 |

TABLE 1-continued

| | |
|---|---|
| Umbilical Flow System | 11 |
| Processor | 16 |
| Second Preferred System | 19 |
| Definitions | 19 |
| Heart Dynamics and Terminology | 24 |
| Methods and Use | 25 |
| fetal circulatory system 30 | 25 |
| placenta 32 | 25 |
| umbilical cord 36 | 26 |
| umbilical vein 38 | 26 |
| umbilical arteries 40 | 26 |
| acoustical signals 51 | 27 |
| target area 59 | 28 |
| * * * (End of Table 1) * * * | |

First Preferred System

FIG. 1 shows a fetal monitoring system 10 constructed according to a preferred embodiment of the present invention. System 10 advantageously allows monitoring of the condition of a fetus using sensed cardiac functions. The cardiac functions are preferably sensed in a manner which is passive and does not require the intentional impingement of ultrasonic energy or other invasive energy sources directly upon the fetus. The cardiac functions are also preferably sensed in a manner which allows the mechanical actions of the fetal heart to be sensed to achieve good timing data on heart functions.

System 10 preferably includes at least one heartbeat sensor 12 for sensing fetal heartbeat information. There may alternatively be a plurality of heartbeat sensors 12.

System 10 also preferably includes at least one umbilical flow detector 14 for detecting the flow of blood within the umbilical cord and providing umbilical blood flow information therefrom.

Fetal monitoring system 10 further includes at least one processor 16. Processor or processors 16 is or are connected to receive the fetal heartbeat information from heartbeat sensor 12. Processor 16 is also connected to receive umbilical blood flow information from the umbilical flow detector 14. The processor 16 derives from the fetal heartbeat information and the umbilical blood flow information at least one fetal health parameter.

FIG. 1 also shows a suitable memory 18 which is used with or forms part of processor 16. Memory 18 can advantageously be formed of one or more types of memory devices, such as read only memory (ROM), random access memory (RAM), read-write memory of various types, and combinations of these or other types of memory. The memory is advantageously provided with the capabilities for storing both initial programming information used to operate the processor and related functions, and for storing data which is collected from the sensor or sensors 12 and detector or detectors 14. Memory 18 can be used to store a variety of preprogrammed tests or analyses which can be run by system 10. Memory 18 can further be used to store processed information and various analytical results which are processed and derived using the sensed information gathered from sensor 12 and detector 14. To best accomplish these functions it may be desirable to use multiple memory devices of differing types.

Heartbeat Sensor

System 10 includes at least one fetal heartbeat sensor 12 for detecting various aspects of the fetal heartbeat. In one form of the invention the heartbeat sensor is advantageously a fetal heart sound sensor, such as an acoustical sensor which senses fetal heart sounds.

In another form of the invention the heartbeat sensor includes a plurality of acoustical sensors which are formed into an array for sensing the fetal heartbeats. The array of sensors can be used in tracking the fetal heartbeats in order to recover preferred measurement data in a continuous fashion despite fetal movement. This also may allow data to be compiled which indicates fetal position with time so as to serve a fetal movement tracking function.

The acoustical sensor or sensors are preferably configured and positioned to receive acoustical sounds or vibrations generated by the fetal heart which pass through the expectant mother's abdomen. Such sounds or vibrations provide fetal heartbeat information.

In another form of the invention the heartbeat sensor is a heart sound sensor in the form of an ultrasound system. The ultrasound fetal heart sound sensor will typically include an ultrasound emitter which is beamed toward the umbilical cord to produce reflected ultrasound waves in the well-known manner. The ultrasound waves are at a high frequency and interfered with or added to by the acoustical vibrations or other actions associated with the fetal heart valves and their associated sounds. The ultrasound waves are reflected by tissues through which the fetal heart sounds are coursing. The ultrasound waves reflected in such tissues are modulated by the interference with the heart sounds and thus produce differences in phase shift of the ultrasound waves which can be sensed and translated into fetal heartbeat information. The ultrasound pickup or sensor produces signals which are passively sensed. The sensed signals are passed through a suitable ultrasound processor to derive fetal heartbeat information therefrom. The output of the ultrasound processor may directly provide the desired information or can be adapted to discriminate fetal heartbeats and other desired fetal heartbeat information which will be described more fully below. A variety of ultrasound systems are commercially available which can be used to sense fetal heartbeat information.

Systems according to this invention can also include a plurality of such ultrasound heartbeat sensors. This can be used to sense fetal heartbeat information for a greater variety of positions which the fetus may assume within the womb. Plural ultrasound heartbeat sensors may also be used similar to the acoustic sensors to provide tracking of fetal positioning, such as described above.

From the sensed fetal heartbeat information, the preferred system discriminates or calculates several types of pertinent and desired information. One desired type of information is the fetal heart rate. The fetal heart rate is easily derived as the inverse of the measured fetal heartbeat period. The fetal heartbeat period is a period of time between successive incidents of the first heart sound. Additional explanation of heart dynamics is provided below.

Figure 4:
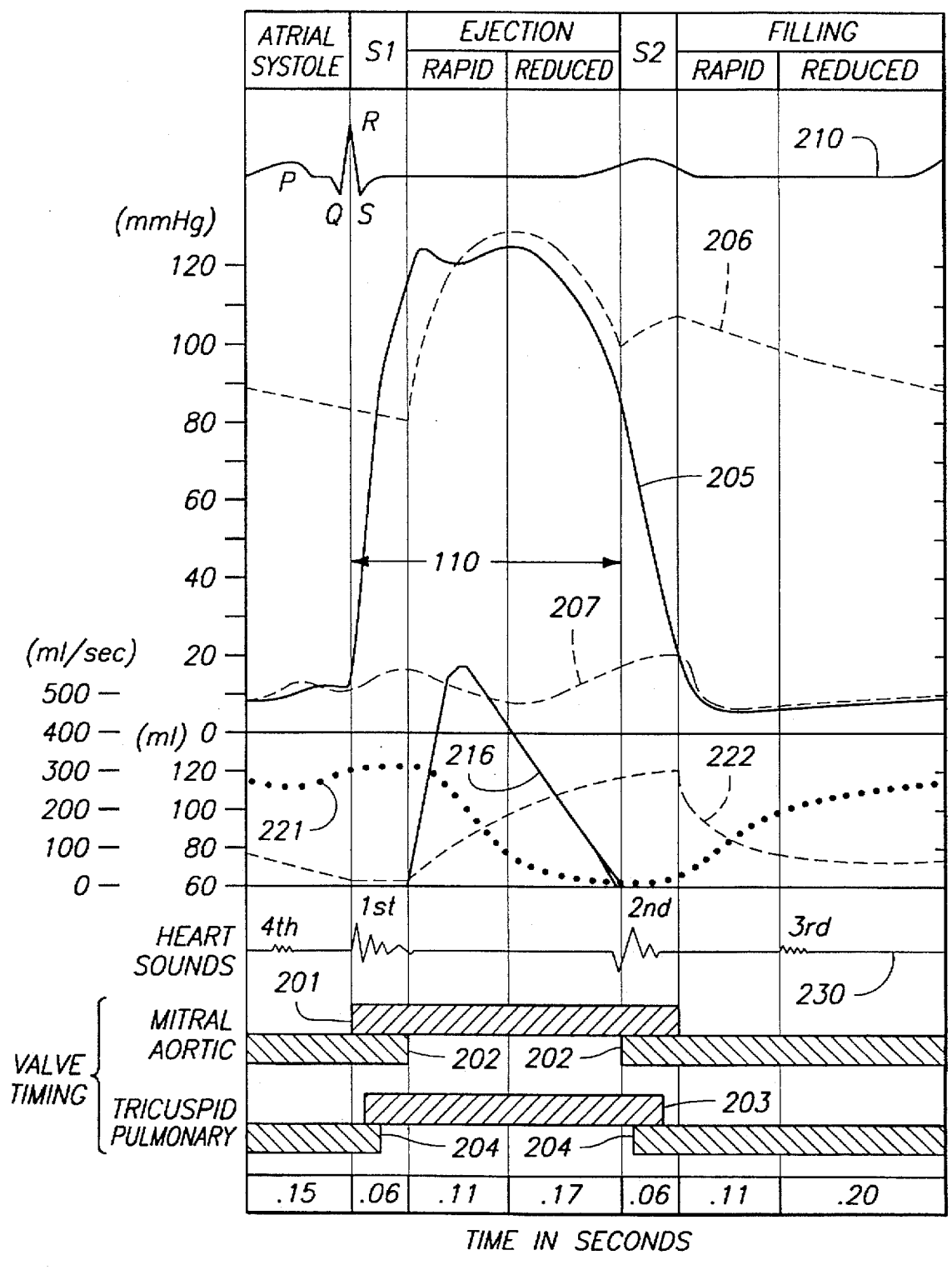
FIG. 4 is a diagram showing various heart functions and approximate timing and flow information relating thereto.

Another desired type of fetal heartbeat information is the period of systole. FIG. 4 shows a number of different heart functions including the period of systole 110. The period of systole is the time period from the start of the first heart sound until the start of the second heart sound. The first heart sound is frequently referred to as the S1 heart sound. The second heart sound is frequently referred to as the S2 heart sound. In more common terminology, the heart produces a "lub-dub" dual tone sound. The first heart sound is the "lub" portion and the second heart sound is the "dub" portion.

Also pertinent is sensing of the second fetal heart sound, which is measured as is described in more detail below. Heartbeat information sensed by heartbeat sensor 12 is communicated to processor 16 for suitable processing in accordance with the preferred methods described below. A suitable fetal heartbeat sensor is one which advantageously enables sensing of the fetal heart rate, while minimizing unwanted acoustical noise, such as a maternal heartbeat, which is or may be present.

Another advantageous characteristic of a preferred fetal heartbeat sensor is the ability to discriminate between the produced frequencies of a fetal heartbeat, and other frequencies which are indicative of unwanted noise. A further advantageous characteristic of such fetal heartbeat sensor is the ability to distinguish, relative to the fetal heartbeat itself, subtle variations or changes in the fetal heart rate or heartbeat. For example, the respective sound frequencies produced during the systolic and diastolic periods have different characteristics or variations. Preferably, the fetal heart rate sensor detects such characteristics or variations for subsequent processing by the fetal monitoring system. System 10 may be advantageously programmed to recognize such frequency variations as correlating to a wellness condition which is or should be recorded or reported. Additionally, an array of passive fetal heartbeat sensors allow continuous tracking of fetal heart sounds even though the fetus is moving.

Heartbeat sensor 12 has been described as an acoustical sensor or sensors, or an ultrasound sensor. It will be readily apparent to those of skill in the art that alternative types of fetal heartbeat sensors may be suitable for use in substitution or combination with the sensors described above. Such other types of sensors are described in my U.S. Pat. No. 4,781,200, the disclosure of which is expressly incorporated herein by reference. It is also noteworthy that in general it is believed that sensors which detect electrical impulse information are not suitable for use in this invention. Current EKG-type sensors do not indicate the period of systole, the duration of the S1 sound, and possibly other desired data, with sufficient resolution to allow successful implementation of the desired analyses explained hereinbelow. Although such limitations appear to exist in electrical impulse sensing systems of which I am aware, systems hereafter developed may allow discrimination of desired heartbeat information and may therefore be suitable or desirable for use in this invention as fetal heartbeat sensors.

Umbilical Flow Sensor

Umbilical flow sensor 14 advantageously detects umbilical flow information which relates to the flow of blood within the umbilical cord which extends between the mother and the fetus. The preferred umbilical flow sensors are capable of sensing the velocity of blood flow within the umbilical cord. One preferred type of umbilical flow sensor 14 is an ultrasonic flowmeter. Ultrasonic flowmeters can measure instantaneous blood flow through vessels or arteries using ultrasound according to previously demonstrated and accepted principles. Ultrasonic flowmeters are advantageous because an ultrasonic signal in the form of an ultrasonic wavefront or waveforms can be beamed through the mother's abdomen without requiring direct impingement of the ultrasonic beam at the fetus. Such waveforms are frequently called ultrasonic beams. Systems which provide detection in this manner allow the dynamics of blood flow within the umbilical cord to be detected at a point downstream from the fetal heart, and more preferably distal to the umbilicus of the fetus whereat the umbilical cord attaches to the fetus.

The preferred umbilical flow sensor and associated methods are advantageous because risks associated with intentional direct beaming of ultrasonic energy are reduced because the ultrasound beam does not intentionally need to be aimed directly at the fetus. In this manner the invention has a definite advantage over current ultrasound systems which are used by focusing the ultrasonic beam intentionally at the fetal heart to determine cardiac functions and performance. Further, direct fetal heart focusing requires precise fetal anatomic alignment with a very limited field of insonication angles available for accurate doppler ultrasound study to be obtained. Insonicating the blood outflow tracts from the fetal heart, such as the fetal aorta, also suffer these same limitations. As a result of fetal movement during testing and the hazards of relatively long ultrasound exposure required to achieve such difficult alignment, this approach is rendered impractical.

The current invention has distinct advantages because measurements are taken at distal locations along the umbilical cord. The umbilical cord has a relatively long length and a cylindrical shape. The umbilical cord measurements according to this invention do require precise insonication alignment directed at the cord; however, due to the length and cylindrical configuation the availability of useful approach angles is very high. The cylindrical shape of the umbilical cord allows approach from 360° about the cord. This must be contrasted to prior techniques which typically have a unique angle of insonication which makes it extremely tedious to gather data and impractical for routine fetal monitoring.

The umbilical cord also does not experience the degree of movement demonstrated by the fetus and other blood vessels contained within the fetus. The umbilical cord is relatively stationary because the cord is anchored to the non-moving maternal placenta and is a floating structure removed from the active fetus. The typically stationary condition of the umbilical cord facilitates accurate measurement and reduces interference with data measurement which are extremely difficult when using previously known procedures.

These factors indicate that the novel procedures of this invention are significant in providing greater opportunity to accurately insonicate and obtain desired flow measurements indicating the ballistics of blood boluses moving along the umbilical arteries. The distal measurements taken from the target location along the umbilical cord are preferable translated into estimates of the actual fetal heart performance which occurs at proximal positions within the fetus. The performance parameters assessed therefrom provide improved assessment of fetal health.

One particular type of ultrasonic flowmeter is able to measure blood flow profiles. One type of blood flow profile is a velocity flow profile which provides an indication of the velocity of blood ejected from the fetal heart which is being conveyed along the umbilical cord. A velocity flow profile is a measure of blood flow velocity through the umbilical cord blood vessel over a given period of time.

Another type of blood flow profile of interest in this invention is a combined velocity and deceleration flow profile. This type of blood flow profile detects both the velocity over time and an associated deceleration rate as the blood flow is slowing within the umbilical cord vessel. This is best visualized by considering the dynamics of the fetal heart which produces a bolus of blood for each ejection cycle. The heart outputs this bolus of blood and the bolus proceeds down the umbilical cord. The bolus is accelerated as it leaves the fetal heart. The accelerating bolus of blood has an effective center which reaches a maximum velocity at some point and time soon after leaving the fetal heart. Thereafter, the bolus of blood decelerates from the point and time of maximum velocity. The umbilical flow detector will in general be directed at the umbilical cord so as to detect the bolus of blood after the point of maximum velocity. The umbilical flow detector preferably is able to detect both the velocity and rate of deceleration of the blood bolus. This information is then used in providing improved analyses of fetal health as explained in greater detail below.

A preferred umbilical flow detector is an ultrasonic flowmeter. One suitable and preferred umbilical flow detector is a gated, pulsed-wave Doppler ultrasonic flowmeter which is configured for providing a measure of blood flow velocity through at least one of the fetal umbilical arteries described below. The preferred umbilical flow detectors are also preferably configured or constructed so as to detect the deceleration rate of the blood bolus.

Some of the suitable Doppler ultrasonic flowmeters operate in a radar-like mode and include a transmitter which is excited with a short, brief burst of ultrasound which forms the stimulation signal. The stimulation signal is in the form of a sound wave or series of sound waves. The sound wave or waves travel effectively as a single packet, spurt or burst. The packet of waves moves toward the umbilical cord extending between the fetus and the mother.

The transmitter typically includes an ultrasound transducer which also serves as a receiver. Alternatively, separate senders and/or passive receivers are clearly possible. Reflections from the umbilical cord are received a short but clearly measurable time later. The ultrasound detector sends out repeated packets of waves and thus senses over time the dynamically changing flow within the umbilical cord. The time delay between the transmission packet and reflected packet is an indication of distance to the target position on the umbilical cord. By examining the Doppler frequency shift at various points in time, a velocity profile with time can be determined. Because the packets of ultrasound waves are provided in closely timed succession, the arrival and traversal of the blood bolus can be detected at the target location along the umbilical cord. The closely timed packets of ultrasound also allow the velocity of the blood bolus to be detected at two or more closely spaced positions along the umbilical cord. This information is used to determine a deceleration rate of the bolus as it proceeds down the umbilical blood vessel.

Other types of umbilical flow detectors may alternatively be used. The desired information preferably indicates at least the velocity of the umbilical blood flow over time, and more preferably both velocity and deceleration of the blood bolus. Alternative detectors may not necessarily employ the same blood flow detection techniques as described above, but may provide information of umbilical blood flow which is indicative of fetal heart inotropic output function.

Processor

Processor 16 is preferably a programmable microprocessor which is or may be programmed to integrate or otherwise analyze fetal heart rate and acoustic or sonar interaction information and umbilical flow information received from sensors or detectors 12 and 14. The sensed or detected information is analyzed to provide at least one fetal health parameter such as described in detail below. One possible implementation of processor 16 is a multi-purpose data processing unit, such as a computer commonly used for a variety of data processing functions and having internal memory.

FIG. 1 also shows a suitable programming device 20 which permits a user to interface with processor 16 and allows a user of system 10 to program the system to perform a variety of diagnostic and analytical tests on data or information received from sensors 12, 14. The results of the diagnostic and/or analytical tests may then be output to a suitable destination. Such destinations include a user-observable display 21 or other appropriate devices, such as an additional processor (not shown) for subsequent processing or data storage devices (not shown).

The preferred elements of above-described system preferably work together, in concert, to monitor and report, among other things, the condition or a change in condition of the fetus. In particular, the fetal health parameter derived from the monitoring system 10 can provide information indicating cardiac health or wellness of a fetus being carried within a mother. The health parameter can also be indicative of fetal health relative to conditions which are more general than just cardiac function. For example, the acceleration of fetal heart rate occurs in response to stimulation by catecholemines, such as adrenaline. If there are various abnormal conditions existing in the fetus which cause stress upon the fetus and provide a continuous or non-continuous but excessive stress response in the form of catecholamine production, then fetal heart rate excursions to higher heart rates may be difficult to achieve for the fetus to achieve. This difficulties may be accompanied by relatively poor associated blood output function. The blood output function can be an inotropic indicator of fetal health, in particular a catecholamine driven indicator of fetal health, and should in a healthy fetus generally show increased capability in response to increasing heart rate. The heart rate is a chronotropic indicator of fetal condition, but is limited in value as current technology has allowed detection and analysis. Adding and combining the chronotropic indicator with contemporaneously obtained inotropic data is of enhanced diagnostic value as allowed by the invention taught herein. To provide increased information and analytical benefits, the fetal heart rate information sensed by the fetal heart rate sensor or sensors, and the umbilical flow information detected by the umbilical flow detector or detectors are provided substantially contemporaneously to processor 16 so that processing may take place in accordance with the preferred methods described below. Other processing regimes are also alternatively possible.

Second Preferred System

Figure 2:
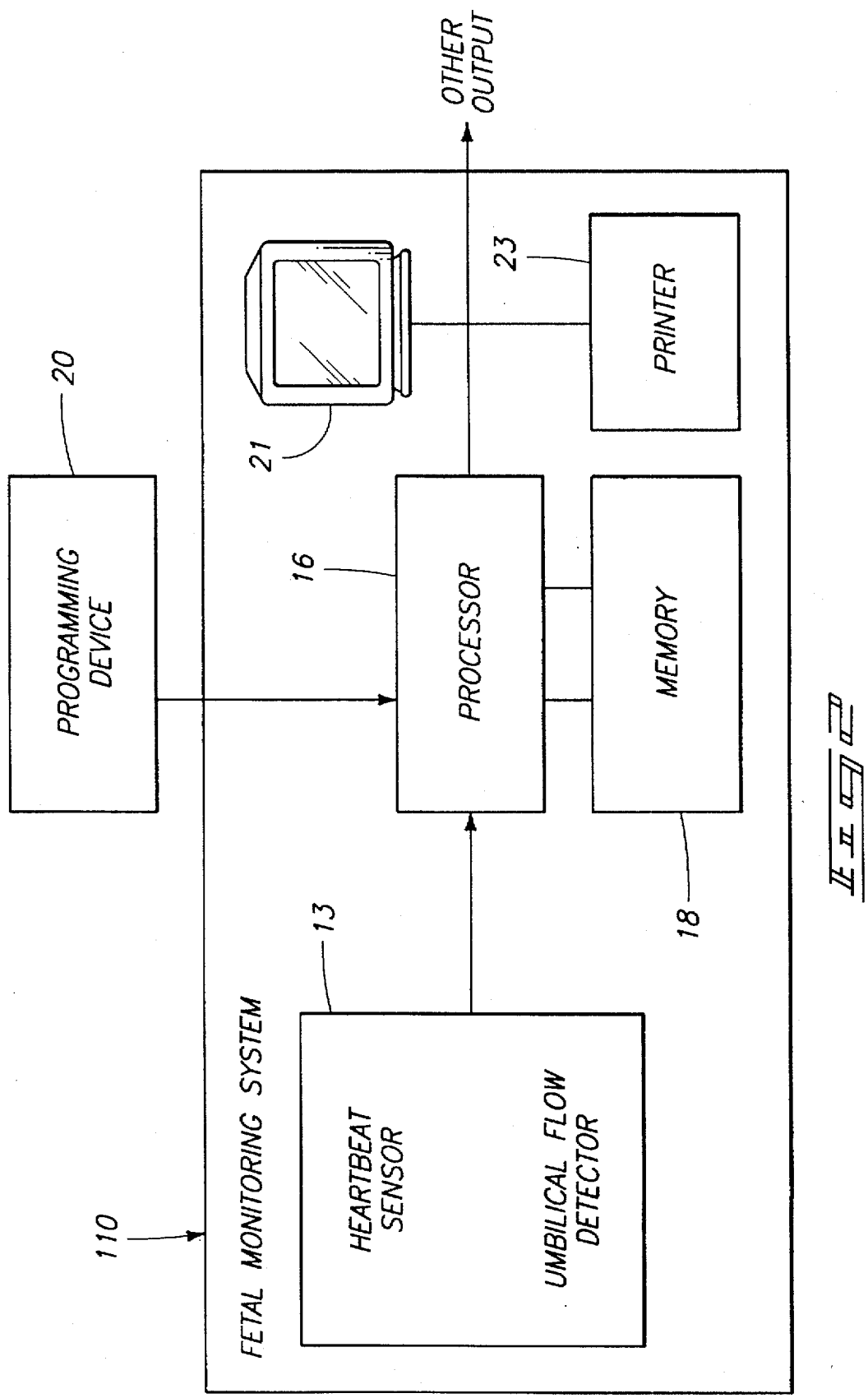
FIG. 2 is a block diagram of a second embodiment system according to the present invention.

FIG. 2 shows a further alternative system 110 similar to system 10 described above. Many of the components described above are the same or similar and such components have been numbered using the same reference numerals.

System 110 differs from system 10 in that the heart beat sensor 12 and umbilical flow detector 14 have been replaced by an ultrasonic detector 13. Ultrasonic detector 13 performs both of these functions. The ultrasonic detector is a subsystem similar to that described above in connection with detector 14. The detector also is provided with any additional signal processing electronics needed to also directly detect fetal cardiac function which discriminates systole, diastole, the first heart sound, the second heart sound and preferably other fetal cardiac functions as described herein.

Definitions

To aid in understanding, some pertinent terms are defined below. Additional explanation may be provided elsewhere herein which aids or adds to the stated descriptions given below. Some of the terms are illustrated in connection with FIG. 4. FIG. 4 shows a number of different cardiac functions and approximate numerical values. Although the specific values may not be valid for all hearts and may not be valid for fetal heart functions, the operation and dynamics of heart operation are illustrated. FIG. 4 includes a series of graphs which are combined for improved presentation and easy understanding of concomitant operative relationships.

S1—The first fetal heart sound occurs for each heartbeat and is sometimes referred to as the "lub" component of the "lub-dub" composite heart sound. FIG. 4 shows the period S1 and indicates that it has a definite period of time which can vary from beat to beat and between individuals.

S2—The second fetal heart sound or "dub" component is S2. FIG. 4 shows the period S2 and indicates that it has a definite period of time which can vary from beat to beat and between individuals.

S1 Terminus—The last acoustic components of the S1 sound signals when the blood bolus begins to leave the heart.

S1 Duration—S1 has a beginning and ending which defines an associated time period. The time interval between such beginning and ending is the duration of S1. This period can act as an estimate of the pre-ejection period. The pre-ejection period is a component of the systolic time interval. The S1 period is also equal to the period termed isovolumetric contraction.

Ejection Time—The time between S1 terminus and the beginning of S2. The ejection time can also be considered as divisible into a rapid ejection portion where pressure is generally building and a reduced ejection portion wherein the pressure is decreasing.

Systole—The time during which the heart generates a contractile force. A portion of systole involves the isovolumetric contraction without blood ejection and another portion of systole involves actual ejection of blood from the heart out through the aorta. The period of systole is from the beginning of S1 to the beginning of S2.

Diastole—The time during which the heart receives blood following its ejection event. It is from the beginning of S2 to the beginning of S1.

S1:S2—This is a ratio of event time periods which can change with heart rate and altered blood loading conditions.

Isovolumetric Contraction Period—The time during which pressure builds up in the heart as muscles contract but before it ejects the blood. The duration of this period normally shortens with increasing ejection contractility. It equals the S1 duration.

Acceleration Time Period—The time from S1 terminus to when the peak or maximum velocity (Vmax) of blood flow is imparted to the ejected bolus of blood by the contracting fetal heart.

Transit Time Period—The time from S1 terminus to when Vmax components' arrive at an arbitrary umbilical artery site. The arbitrary site is determined by the target location on the umbilical cord artery where velocity is measured by the doppler velocimetry unit or other umbilical flow detector. The umbilical flow detector also preferably measures both the rate of deceleration and velocity of the ejected blood bolus at this point.

Pulse Velocity—The velocity of a pressure wave developed by the ejecting heart can be detected by the umbilical flow detector, such as in the form of an arterial expansion event of the umbilical blood vessel. This expansion precedes its associated bolus arrival. This measurement can be used for timing purposes to indicate or confirm timing of heart dynamics and detected blood flow downstream in the umbilical cord.

Mean Aortic Acceleration—This is derived from measurements and is an indication or estimate calculated as the maximum velocity (Vmax) divided by the acceleration time period. It serves as an index of fetal heart inotropism. This is one of the most preferred fetal assessment parameters.

Acceleration Rate—This is a term estimating the ratio of fetal cardiac acceleration time period to ejection time period. The resulting ratio is an indication of inotropism. This is one of the most preferred fetal assessment parameters.

Ejection Fraction—This is a measure or estimate of the fraction calculated as fetal blood volume ejected during each beat over the total blood held within the fetal heart when filled. It is correlated with the mean aortic acceleration and reflects on fetal cardiac performance.

Stroke Volume—This is a measure or estimate of volume of blood ejected by heart with each beat. It varies and is correlated to values of Vmax.

Tension-Time Index (TTI)—This is estimated by the product of: ejection time times Vmax (or portions thereof) times fetal heart rate. It is a derived parameter which can be used to indicate fetal heart oxygen consumption rates, and other aspects of fetal cardiac activity.

Pressure-Rate Product (PRP)—This is a parameter estimated by the product of Vmax (or portions thereof) times fetal heart rate. It can be related to fetal heart oxygen consumption rates. The use of consumption rates tied to inotropic and cardiodynamic markers enables inferences regarding fetal economy of cardiac functioning.

Fetal Heart Rate (FHR)—Fetal heart rate is the rate at which fetal heartbeats occur. The period between fetal heart beats is the beat-to-beat period and is the inverse of the fetal heart rate. Changes in fetal heart rate can be spontaneous or induced and can be either of the acceleration, static or deceleration types.

Baker Inotropic Adaptation Score (BIAS)—This is a derived parameter which is an assessment of the degree to which one or more inotropic indices deviate from baseline values during associated changes in fetal heart rate versus baseline fetal heart rate, sometimes referred to as fetal heart rate (FHR) excursions. The degree of deviation and temporal sequence of deviation of inotropic and Vmax values during FHR excursions allows the scoring of fetal inotropic levels and provides an indication of cardiodynamic adaption by the fetus to its environment. The timing of these indices return or recover to baseline values also relates to fetal vigor. The inotropic adaption score can be used in conjunction with the derived parameters tension-time index (TTI) and pressure-rate product (PRP) to provide an indication of fetal cardiac oxygen consumption efficiency values.

Heart Dynamics and Terminology

The upper portion of FIG. 4 shows some of the major aspects of a heartbeat cycle. Across the top of the chart are important phases of the heartbeat. Atrial systole is shown as the first portion of the heartbeat cycle during which the atria of the heart contract and supply blood through the mitral and tricuspid valves to the left and right ventricles. The bottom timing charts 201–204 show operation of the mitral, aortic, tricuspid, and pulmonary valves respectively. During atrial systole the aortic and pulmonary valves are indicated closed by the hatched bars. The mitral and tricuspid valves are open as shown by the open areas adjacent the bars.

The chart of FIG. 4 is primarily directed to showing information concerning output and functioning of the left ventricle. Left ventricular pressure is shown as curve 205 with units read on the left-hand scale at millimeters of mercury (mmHg). The pressure developed in the aorta is shown as curve 206, readable on the same scale. The atrial pressure in the right atrium is shown as curve 207.

FIG. 4 also shows the electrocardiographic response at the top curve 210. The P, Q, R, and S points of the electrocardiogram are illustrated.

FIG. 4 further shows the left ventricle outflow or discharge at curve 216. The approximate units are indicated at the first left scale in milliliters per second (ml/s). Blood output of the left ventricle occurs after S1 terminus and prior to S2 during which the aortic valve is open and the mitral valve is closed.

FIG. 4 still further illustrates the approximate volume of the left ventricle as curve 221 and the volume of the left atrium as curve 222. These curves refer to the second scale at the left and are expressed in milliliters (ml).

The primary heart sounds are the first heart sound which occurs during S1 and the second heart sound which occurs during S2. The third and fourth heart sounds are also shown in FIG. 4. Curve 230 of FIG. 4 shows an exemplary acoustical output function.

If excessive oxygen consumption is occurring for a particular level of cardiac contractility, a component of fetal decompensation or maladaption is present. A minimum of oxygen consumption for a particular level of cardiac contractility suggests a compensated fetus.

Methods and Use

To assist in understanding the preferred methods and use of the present invention, a short discussion of the fetal circulatory system follows.

Figure 3:
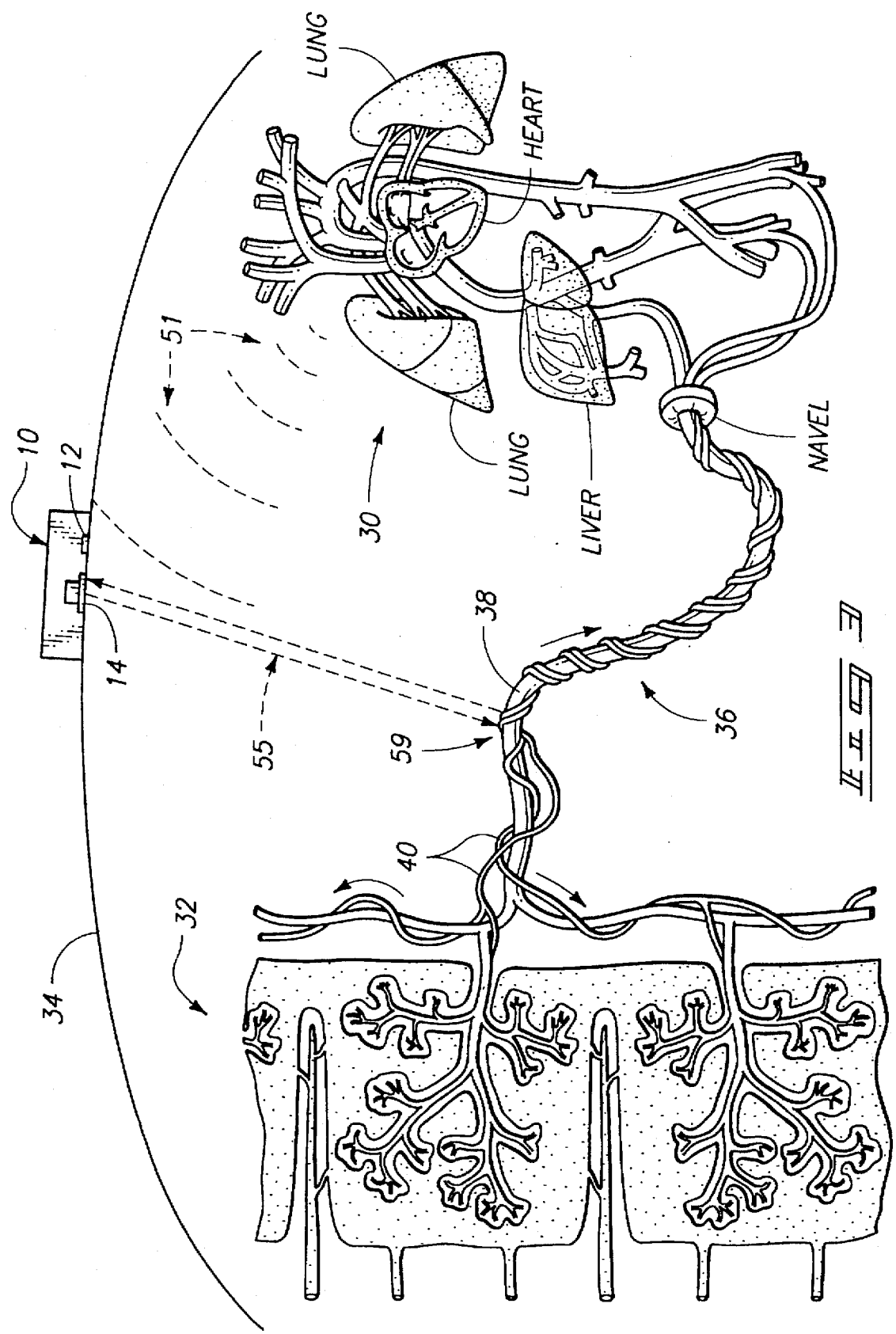
FIG. 3 is a diagram showing the system of FIG. 1 in use adjacent a maternal abdomen in accordance with the preferred methods, and the interrelation of a fetal circulatory system and placenta.

FIG. 3 illustrates the interrelation between a fetal circulatory system 30 and the placenta 32. The circulation of blood through a fetus is different from that of a newborn infant. Respiration, the procurement of nutrients, and the elimination of metabolic wastes occur principally through the maternal blood. In many respects the functioning of the organs of the fetus are modified to better accommodate the fetus's condition within the womb and to take better advantage of the fetus's connection with the maternal placenta. The exchange between the maternal and fetal blood circulations occurs across partitioning membranes located within placenta 32. The transport membranes are fed by capillary networks on both sides of the membranes. The networks and membranes maintain the maternal and fetal blood flows separate, but allow migration of blood constituents between the two blood flows.

FIG. 3 shows that the umbilical cord 36 connects the fetal circulatory system 30 and maternal placenta 32. Umbilical cord 36 includes one umbilical vein 38 and two umbilical arteries 40 surrounded by a gelatinous substance. Oxygenated and nutrient-rich blood flows through umbilical vein 38 toward the fetus. Deoxygenated blood is returned from the fetus to placenta 32 by umbilical arteries 40.

FIG. 3 also shows system 10 of FIG. 1 positioned appropriately adjacent maternal abdomen 34 for sensing fetal heart rate information and umbilical flow information in accordance with the preferred methods. Although system 10 is depicted as separate elements comprising system 10, i.e. sensor 12 and detector 14, systems which perform these function using the same equipment are also possible.

Methods according to the invention advantageously include placing at least one fetal heart sensor at an appropriate location or locations upon the maternal anatomy to sense fetal heartbeat information. The preferred acoustical sensors are advantageously placed upon the maternal abdomen for sensing acoustical signals 51 emanating from the fetal heart.

Figure 5:
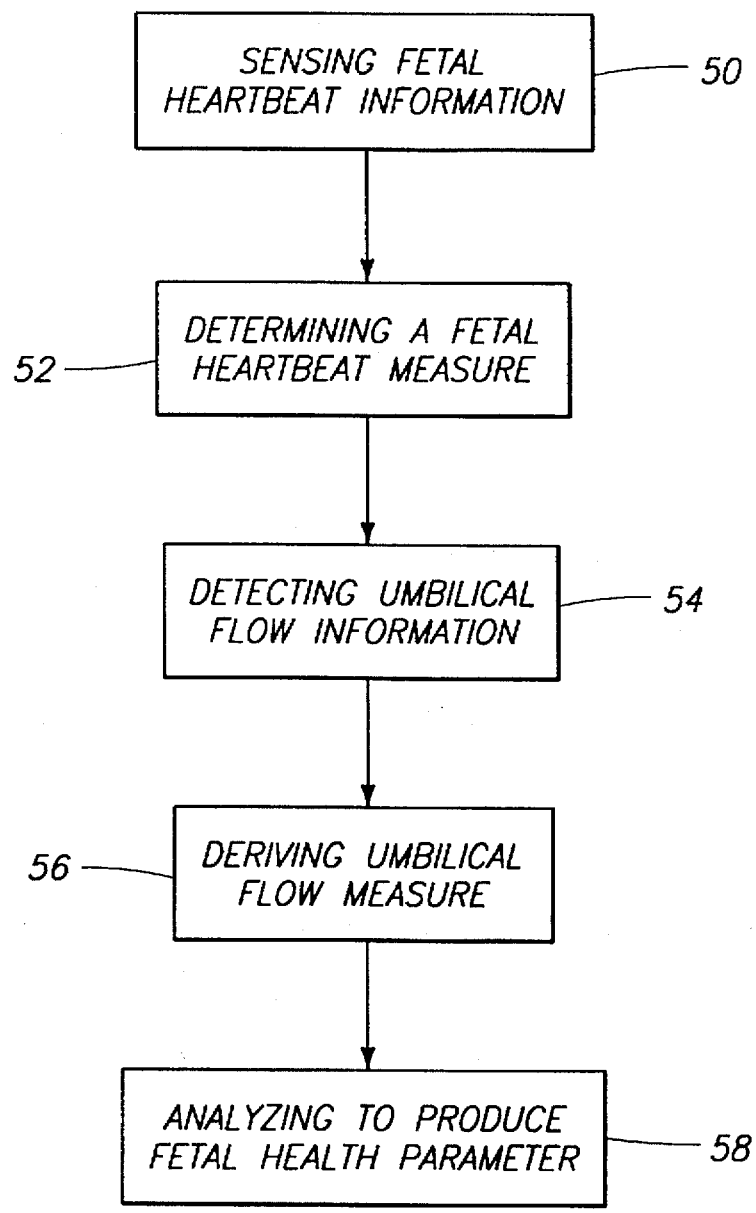
FIG. 5 is a block diagram which illustrates one preferred method of the invention.

The methods also preferably include sensing fetal heartbeat information using the at least one fetal heart sensor, such as sensors 12 or 13. FIG. 5 illustrates this sensing step. The sensing includes sensing at least the first fetal heart sound which is associated with the S1 period. The terminus of the first fetal heart sound indicates the starting time for consideration of the flow of a bolus of blood which is displaced from the fetal heart and which travels down the umbilical arteries toward the placenta 32. The bolus of blood is accelerated from a stationary condition within the ventricles of the fetal heart. In the fetal heart both ventricles expel blood which passes through the descending aorta and into the umbilical arteries.

The sensing of fetal heartbeat information is advantageously accomplished on a real-time basis. This is preferred to give the necessary timing point origin relative to the blood boluses which move down the umbilical cord arteries at delayed speeds and intervals.

The sensing of fetal heartbeat information also preferably includes sensing the second fetal heart sounds which are associated with the S2 period. The sensing of the second fetal heart sounds or otherwise sensing the S2 period allows the ejection time period to be determined. Other fetal heartbeat information in lieu of or in addition to the fetal heartbeat period, fetal heartbeat frequency, and fetal heart ejection time period may alternatively be derivable from the sensed fetal heartbeat information.

The sensing also provides an indication of the timing of the fetal heart functions for purposes of determining the transit time period between the fetal heart and the target area 59 where the umbilical flow detector 14 detects information about the flow of blood within the umbilical cord 36.

From the sensed heartbeat information, at least one fetal heart rate measure is determined (step 52). Preferred fetal heart measures include duration of the real-time beat-to-beat fetal heartbeat cycle, fetal heart rate, duration of S1, duration of S2, and duration of systole. Other preferred heart rate measures include fetal heart rate acceleration and deceleration. Such fetal heart rate acceleration or deceleration events may be in response to stimulus events or conditions, such as fetal acidosis, hypoxia, asphyxia, hypovolemia, or umbilical cord compression to name just a few. Other fetal heart rate measures are also possible.

Preferred methods according to this invention are also performed so that the distal values being measured at the umbilical cord are used as indicators or estimates of the proximal events which have actually occurred in the functions performed by the fetal heart. Distal events are those considered downstream of the fetal heart and within the umbilical cord. The umbilical cord runs from the umbilicus of the fetus to the maternal placenta. Proximal events are those within the fetal heart or vessels adjacent to the fetal heart. Transit times between performance within the fetal heart and the distal values sensed in the umbilical cord are used to link data collected on the events and achieve coordination that will allow measurement and estimation useful in assessing fetal health.

Preferred methods according to this invention also can include positioning at least one umbilical flow detector or sensor at an appropriate position relative to the mother to detect umbilical blood flow information. Such umbilical blood flow information indicates flow of blood within the umbilical cord. Positioning or placement of the umbilical flow detector will vary dependent upon the type and operation of the detector. In general, the preferred umbilical flow detectors will be placed against the maternal abdomen to allow easy monitoring of the fetus without surgical or other involved or relatively invasive technologies. In the operation of the preferred detector 14, the ultrasound beam 55 is directed toward the target area 59 upon the umbilical cord. The preferred ultrasonic transducer is positioned so as to achieve this relationship by aiming the beam and then receiving detected information which allows any adjustments to the positioning and aiming so as to locate the umbilical cord and detect umbilical flow information therefrom.

The preferred methods also include detecting umbilical blood flow information. This is advantageously done using the at least one umbilical flow detector 14 or 13. This step is illustrated at step 54 of FIG. 5. At least one umbilical flow measure is obtained or derived from the step of detecting umbilical blood flow information. Even more preferably, the umbilical flow information relates to blood flow through at least one of the umbilical arteries carrying deoxygenated blood away from the fetus and to the placenta. The umbilical flow information can be ultrasonically obtained information. As shown in FIG. 3, the detecting step is advantageously done in close proximity to maternal abdomen 34 by providing an ultrasonic wave 55 which is propagated to, and then from at least one of umbilical arteries 40. A preferred detector is an ultrasonic umbilical flow detector or flowmeter configured, after appropriate positioning relative to the mother, for ultrasonically obtaining the umbilical flow information. An even more preferred detector is a gated, pulsed-wave Doppler flowmeter, such as that described above.

The detecting step preferably results in acquisition of umbilical flow information which is useful in producing one or more umbilical flow measures. The umbilical flow information obtained is used in a deriving step which results in an umbilical flow measure or measures helpful in monitoring fetal health. The umbilical flow measure or measures is used either directly or indirectly as indicators of the proximal performance of the fetal heart. A preferred umbilical flow measure derived from the detected umbilical flow information includes blood flow velocity through or within the umbilical cord. Another preferred umbilical flow measure is the deceleration rate at which the bolus of blood is slowing as the bolus of blood travels down the umbilical cord blood vessel. The deceleration rate is discernible when the ultrasonic or other detector takes repeated velocity measurements closely spaced in time so that an effective estimate of decreasing flow velocity can be achieved over the target area 59. This deceleration is achievable using know sampling rates of ultrasonic detection systems of the type described above. Other techniques for detecting not only velocity but also deceleration rates may be appropriate.

The detecting and derivation of umbilical flow measures therefrom may also advantageously include derivation of information indicating the pulse velocity. The pulse velocity is obtained from timing of the pulse between the fetal heart and the target zone. As explained above, the pulse velocity is different from the velocity of the bolus of blood that moves down the umbilical cord. The pulse transit time and pulse velocity can be used to help determine or confirm the timing of the fetal heartbeat and the relationship between a particular heartbeat and an associated bolus of blood. The velocity of the blood flow will be slower and can vary to a greater extent than the velocity of the pressure pulse which travels down the umbilical cord in advance of the bolus. Thus additional discriminating information may be used to help derive the transit time for the blood boluses. The pulse wave is detected by the umbilical flow detector 14 or 13.

The methods according to this invention also preferably include analyzing the sensed or detected information to produce at least one fetal health parameter therefrom. The produced or derived fetal health parameter or parameters are intended to be an indicator of at least one or more aspects of fetal well-being. The fetal health parameters may each be a direct indicator of the condition or health of a fetus, or they may be used in combination with other sensed or detected information which combines to provide such an indicator or indicators. The sensed or detected information may also be used with information obtained from another procedure or reference work in order to deduce a fetal health indicating parameter.

FIG. 5 shows at step 58, at least one fetal health assessment parameter is derived or calculated. Preferably, the fetal health parameter which is derived or calculated using at least one of the fetal heart measures determined at step 52, or at least one of the umbilical flow indicators obtained at step 56, or a combination of such measures either alone or used with other factors to improve diagnostic or predictive utility. The deduced fetal health assessment parameter is at least a partial function variable dependent upon at least one of the fetal heart rate measures and/or umbilical flow measures. It is also often a function variable over time.

In one form, the fetal health parameter indicates, or otherwise gives some measure of fetal cardiac oxygen consumption. Fetal cardiac oxygen consumption is important because it allows health care providers to assess the health of the fetus. In another form, the fetal health parameter indicates the relative inotropic cardiac output or functioning of the fetus as a function of chronotropic cardiac output or functioning. In another form the fetal health parameter can indicate relative stress on the fetus due to one or several conditions. In still another form the fetal health parameter can indicate cardiac influences of catecholamine in the fetal blood. In a further form, the fetal health parameter can indicate general strength and functioning of the fetal heart. In still another form, the fetal health parameter may indicate fetal heart contractility. In another form, the fetal health parameter can indicate fetal cardiac stroke volume. In yet another form, the fetal health parameter may estimate the ejection fraction of the fetal heartbeats and with time.

One such preferred fetal health assessment parameter, a first fetal health parameter, includes a ratio which is derived or calculated using the fetal umbilical artery systolic blood flow velocity and the fetal umbilical artery diastolic blood flow velocity which are determined as part of the flow indicators obtained at step 56 (FIG. 3). One preferred ratio is a ratio of umbilical artery systolic flow velocity to diastolic umbilical artery flow velocity. Another useful ratio is the ratio defined as the difference between the maximum systolic umbilical artery flow velocity and the diastolic umbilical artery flow velocity divided by the systolic umbilical artery flow velocity. Other ratios and calculations are possible.

Other fetal health parameters can also be used to assess the health of a fetus. Another such parameter, second fetal health parameter, is an index which relates to or is approximately indicative of fetal cardiac oxygen consumption. This is done in the following way. The parameter can be calculated from the product of: a) the duration of systole; b) the heart rate; and c) an index of maximum fetal heart ejection blood flow velocity. Both the duration of the systole and the heart rate are ascertained as a fetal heart rate measure, such as from the acoustical sounds produced by the fetal heart and sensed by the heart rate sensor 12 or 13 as discussed above. The determination of a fetal health parameter may be calculated by using measurements at two or more points in time and calculating a ratio of baseline (rest) conditions to workload (stress) conditions. The index of fetal blood flow velocity is preferably calculated using a statistically significant sampling of Vmax values measured as explained further below.

Another and third fetal health parameter which can be deduced relates to myocardial oxygen consumption and contractility. Myocardial contractility refers to the strength of a ventricular contraction during which blood is ejected from the heart. This parameter may be described by a product which includes as primary variables the fetal heart rate and the velocity of the fetal heart blood flow, preferably in the form of a sampling of Vmax values as explained below. This parameter can best be ascertained at two or more times to develop both a baseline and current condition so that health and health changes can be assessed at two or more times for purposes of comparison, analysis and assessment of both values and variability.

One advantage of using such parameters is that such data enables a health care provider to more closely assess and monitor so-called fetal cardiodynamics as an expression of fetal neurologic competence. More specifically, changes in the fetal cardiac system, such as heart rate accelerations and decelerations events, are predicated on a healthy fetal Autonomic Nervous System (ANS) interacting with a stable fetal cardiovascular system. The fetal ANS detects events, such as acidosis, umbilical cord compression, hypovolemia, and/or hypoxia and, in turn, relays inputs to the fetal cardiovascular system which stimulates appropriate adaptations designed to resolve or address the detected event. Two so-called effector arms of the ANS are the Sympathetic Nervous System (SNS) and the Parasympathetic Nervous System (PNS). The Vagus nerve, a PNS nerve, serves to slow the heart rate in response to certain stimuli. The SNS input serves to increase the heart rate, the duration of systole, and the vigor of cardiac contractility in response to certain stimuli. The effects of the PNS (slowing the heart rate) may be thought of as counterbalancing the effects of the SNS (increasing the heart rate). A coordinated interplay of the SNS and PNS is best exhibited by a healthy, beat-to-beat fetal heart rate variability which may be measured. Because fetal SNS cardiac nerve fibers (responsible for producing neurogenic SNS input) are immature and not as well developed as the vagal fibers (responsible for producing the PNS input), the SNS has been equipped with a special augmenting humeral support system. The humeral support system is in the form of a humeral catecholamine production from the fetal adrenal gland. Catecholamines are groups of regulatory molecules which are responsible for increasing myocardial contractility, stroke volume, and heart rate to name just a few. Current fetal heart rate monitoring techniques do not sense such humeral sponsored events beyond heart rate increases. The above system and methods enable these and other valuable humeral sponsored parameters to be obtained.

Using the fetal heartbeat measure or measures and the umbilical flow measure or measures described above, an assessment as to the sympathetic nervous system (SNS) and its impact on fetal well-being may be determined. For example, one well-known effect, a so-called Bowditch effect, is demonstrated where there is increasing myocardial inotropy accompanying an increasing fetal heart rate. In this context increased myocardial contractility is an increase in volume of blood ejected from the fetal heart per stroke. The counterpart of the Bowditch effect is the Woodworth effect which shows a decreasing myocardial inotropy despite an increasing heart rate. Determining when and how a fetus demonstrates transition between a relatively more healthy cardiac functioning demonstrating the Bowditch effect to a relatively less healthy cardiac functioning demonstrating the Woodworth effect, gives insight into diagnosing fetal health and can be used in managing fetal health in-utero. This provides a fourth fetal health assessment parameter useful in the invention. The contractility is thus measured or indicated by the measurement of Vmax as described below.

In addition, the etiology or cause of apparent umbilical cord conditions can be identified. For example, worrisome variable fetal heart rate decelerations in conjunction with bradycardia (a cardiac rate which is slower than a predetermined rate) can result from either benign fetal head compression or from a more serious cord compression. The two fetal health parameters explained above may be useful to help distinguish differences between the two so that appropriate management strategies and treatment protocols can be implemented. A benign fetal head compression can cause intense vagal activity, which in turn, causes all SNS parameters to fall. A calculated ratio of the second fetal health parameter described above to the third fetal health parameter which is followed from baseline (rest) to stress zones would indicate this situation by having an identifiable value of less than 1. However, with a more serious cord compression, the heart would compensate by extending its duration of systole (the period during which blood is expelled from the heart) to overcome the blockage. As a result, the calculated ratio of the first to PRP followed from baseline (rest) to stress zones would indicate this situation by having an identifiable value of greater than 1. Thus, the cord pinching will reduce the blood flow velocity parameter which was substituted for the pressure readings. As a result, the heart's compensatory contractility efforts to overcome the blockage with pressure will be masked. However, the lengthened systolic duration parameter in the second fetal health parameter would not be masked. Since the remainder of the products in the second fetal heart parameter which is used as the dividend and the third fetal health parameter which is used as the divisor cancel, the systolic duration is left, which, when used as a ratio from baseline to the stress zone, will become greater than 1.

Figure 6:
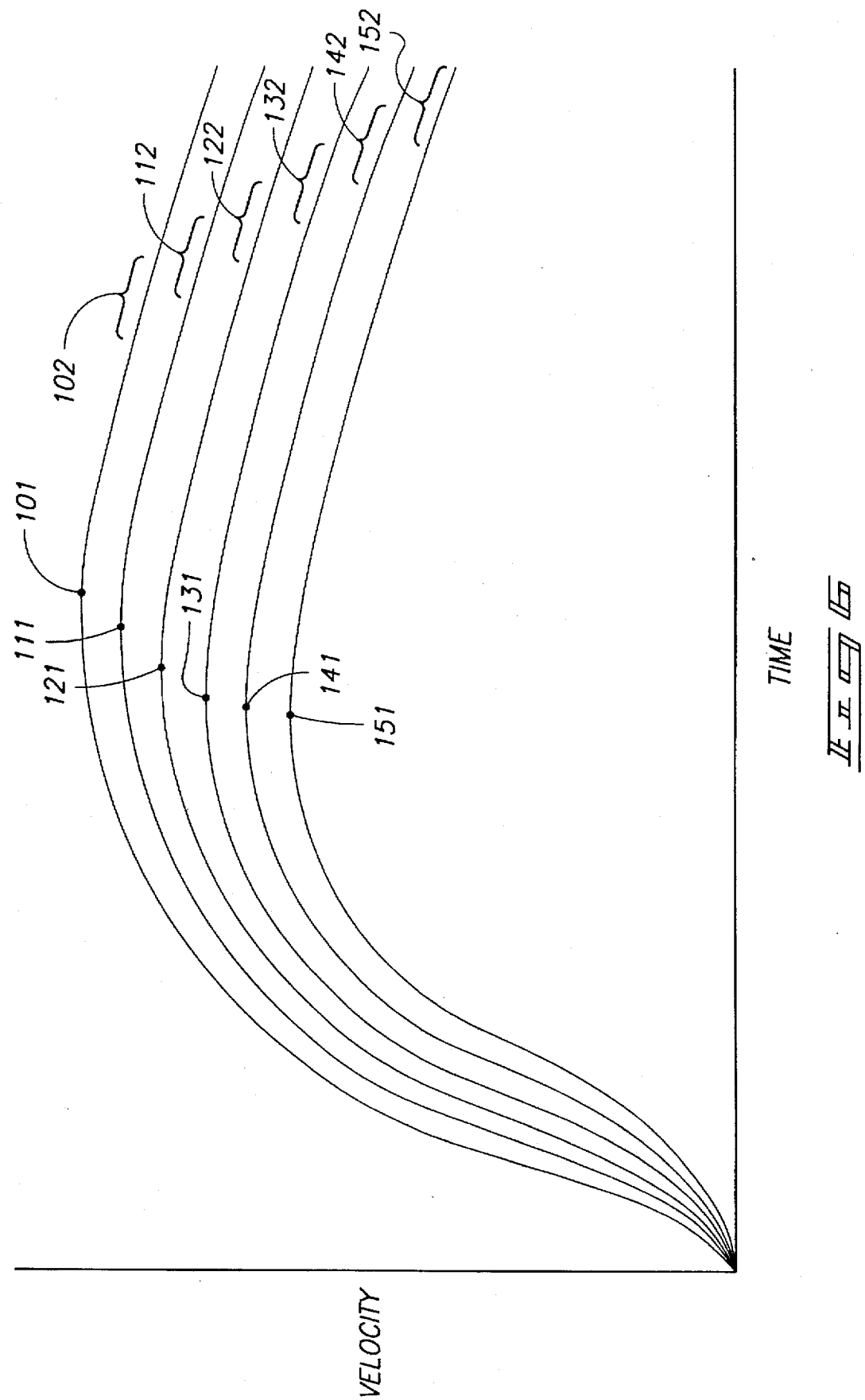
FIG. 6 is a graph plotting velocity as a function of time for a number of different umbilical blood boluses ejected from the fetal heart with different maximum velocities.

FIG. 6 shows six curves having maximum velocity points 101, 111, 121, 131, 141, and 151 associated therewith. The velocity curves illustrate different fetal heartbeats having different velocities and accelerations. The segments 102, 112, 122, 132, 142, and 152 illustrate the target zones 59 wherein the detectors 14 and 13 are able to take one, or more preferably plural velocity measurements. With this information and the added information of deceleration rate, the detected distal umbilical flow information can mathematically be extrapolated to retrogradely determine estimates which are preferred measures of the fetal cardiac ejection events which occur proximally within the fetal heart. For example, the umbilical flow detector detects information characterized by a flow velocity or velocities and a deceleration rate or deceleration rates having specific numerical values. FIG. 6 illustrates merely six different curves, but mathematical relationships can be developed to cover a large number of different possibilities of velocity and deceleration. This are preferably established using empirically derived information.

The information of umbilical cord velocity and deceleration, such as from the preferred doppler detector, are most preferably combined with transit time information which is indicated by the x-axis of the graph shown in FIG. 6. With these pieces of information which are sensed remotely from the fetal heart, the umbilical flow information and sensed heartbeat information can be analyzed to link umbilical vessel ballistics in order to determine measures of fetal cardiac performance. Various analyses can then be performed to provide an analyzing step or steps which indicate the performance of the fetal heart in a number of different ways. Various curve regression and fitting analyses can also be utilized, such as using standard computer programs, to extract various slope, tangent, timing or other relationships which are needed to determine the preferred fetal cardiac measures of predictive value.

In the most preferred methods, such methods are performed at two or more distinct points in time. The methods can be conducted contemporaneously to associated fetal heart rate events. This information allows the physician to establish a baseline performance which indicates a fetal health parameter. This same fetal health parameter can thereafter be assessed again at a later time and then changes in fetal health parameters, fetal cardiac parameters, and other fetal functions can be compared at different times and health changes are indicated by such an analysis.

These are but a few fetal health assessment parameters which are able to be derived in accordance with the preferred system and methods. Other fetal health assessment parameters which are calculable or derivable from the fetal heart measures and/or umbilical flow measures will be apparent to those of skill in the art.

The analyzed fetal health parameter can in some forms of the invention also be output. The output information is or may be output to a suitable medium in order to indicate to a health care provider an indication of fetal health. Preferably, the output information is variable and changes according to the various health scenarios experienced by a fetus. As mentioned above, such information may be output to a suitable visual display 21, printer 23, or to an additional processor for further processing. Other output mediums are possible.

The invention has been described in language more or less specific as to structural, methodological, or other aspects and features. It is to be more properly understood that the invention is not necessarily limited to the specific forms shown and described. Other equivalent structures and features may also be within the inventive concepts which are appropriately protected under the grant of patent rights being sought. The invention is therefore being claimed in an effort to define the invention, but the various forms or modifications which the invention may take is difficult or impossible to define with complete certainty. Judgement must be utilized to properly interpret the scope of protection which is to be applied to protect these new and inventive concepts.

I claim:

1. A method for monitoring to assess at least one fetal health parameter associated with a fetus being carried within an expectant mother, comprising the steps:

placing at least one fetal heart sensor at an appropriate position relative to the mother for sensing fetal heartbeat information emanating from a fetal heart beating within the fetus;

sensing fetal heartbeat information using the at least one fetal heart sensor;

determining at least one fetal heartbeat measure from the fetal heartbeat information;

positioning at least one umbilical flow detector at an appropriate position relative to the mother to detect umbilical blood flow information, said umbilical blood flow information indicating flow of blood within an umbilical cord which extends between the fetus and a placenta carried within the mother, said positioning occurring so as to allow detection of the umbilical blood flow information at an umbilical target location which is distal from a fetal umbilicus whereat the umbilical cord attaches to the fetus;

detecting umbilical blood flow information from the umbilical target location using the at least one umbilical flow detector;

deriving at least one umbilical flow measure from the umbilical blood flow information detected in said detecting step;

analyzing said at least one fetal heartbeat measure and said at least one umbilical flow measure to produce said at least one fetal health parameter.

2. The method of claim 1 and further comprising comparing said at least one fetal health parameter to at least one baseline fetal health parameter measured previously in time in a manner similar to said at least one fetal health parameter to determine at least one fetal health parameter change.

3. The method of claim 1 wherein said determining at least one fetal heartbeat measure includes determining fetal heart rate produced by the fetal heart.

4. The method of claim 1 wherein said determining at least one fetal heartbeat measure includes determining systolic duration of fetal heartbeats produced by the fetal heart.

5. The method of claim 1 wherein said determining at least one fetal heartbeat measure includes determining a period of time associated with the first heart sound produced by the fetal heart.

6. The method of claim 1 wherein said determining at least one fetal heartbeat measure includes determining a period of time associated with the second heart sound produced by the fetal heart.

7. The method of claim 1 wherein said deriving at least one umbilical flow measure includes deriving at least one estimate of fetal blood flow velocity.

8. The method of claim 1 wherein said deriving at least one umbilical flow measure includes deriving at least one estimate of maximum fetal blood flow velocity ejected from the fetal heart.

9. The method of claim 1 wherein said deriving at least one umbilical flow measure includes deriving at least one estimate of fetal blood flow acceleration or deceleration.

10. The method of claim 1 wherein said deriving at least one umbilical flow measure includes deriving at least one estimate of fetal blood flow acceleration associated with ejection of fetal blood from the fetal heart.

11. The method of claim 1 wherein said deriving at least one umbilical flow measure includes deriving at least one estimate of fetal blood flow deceleration associated with deceleration of fetal blood within the umbilical cord.

12. The method of claim 1 wherein said analyzing includes determining mean aortic acceleration.

13. The method of claim 1 wherein said analyzing includes determining acceleration rate.

14. The method of claim 1 wherein said analyzing includes determining a systole acceleration time period which is a period of time for which fetal blood flow from the fetal heart is experiencing an increasing velocity.

15. The method of claim 1 wherein said analyzing includes:

determining a systole acceleration time period which is a period of time for which fetal blood flow from the fetal heart is experiencing an increasing velocity;

determining at least one estimate of maximum systolic velocity which is a maximum fetal blood flow velocity ejected from the fetal heart;

determining a mean aortic acceleration which is the maximum systolic velocity divided by the systole acceleration period.

16. The method of claim 15 wherein said analyzing includes comparing multiple mean aortic accelerations determined at various fetal heart rates.

17. The method of claim 15 wherein said analyzing includes comparing multiple acceleration rates determined at various fetal heart rates.

18. The method of claim 15 wherein said analyzing includes comparing multiple mean aortic accelerations determined at various fetal heart rates to determine a fetal heart rate at which said mean aortic acceleration rate is at a minimal value.

19. The method of claim 15 wherein said analyzing includes comparing multiple mean aortic acceleration determined at various fetal heart rates to at least one baseline mean aortic acceleration rates measured previously in time to determine at least one fetal health parameter change.

20. The method of claim 15 wherein said analyzing includes comparing multiple acceleration rates determined at various fetal heart rates to at least one baseline acceleration rate measured previously in time to determine at least one fetal health parameter change.

21. The method of claim 1 wherein said analyzing includes comparing systolic and diastolic flow velocities detected in said detecting step.

22. The method of claim 1 wherein said analyzing includes comparing systolic and diastolic periods of time.

23. The method of claim 1 wherein said analyzing includes comparing pulse transit times for a plurality of umbilical blood flow pulses.

24. The method of claim 1 wherein said analyzing includes determining an ejection time period which is a period of time during which blood is ejected from the fetal heart.

25. The method of claim 1 wherein said at least one fetal health parameter includes an index which relates to fetal cardiac oxygen consumption.

26. The method of claim 1 wherein said at least one fetal health parameter includes a systole velocity profile which indicates velocity of fetal blood flow over a systolic period; and further comprising comparing said systole velocity profile to at least one baseline systole velocity profile measured previously in time to determine at least one fetal health parameter change.

27. The method of claim 1 wherein said analyzing includes consideration of an inotropic index of performance against a chronotropic index of performance to produce said at least one fetal health parameter which is dependent upon both said inotropic index and said chronotropic index.

28. A method for monitoring to assess at least one fetal health parameter associated with a fetus being carried within an expectant mother, comprising the steps:

determining at least one fetal heartbeat measure from fetal heartbeat information sensed from a fetal heart beating within the fetus;

positioning at least one umbilical flow detector at an appropriate position relative to the mother to detect umbilical blood flow information, said umbilical blood flow information indicating flow of blood within an umbilical cord which extends between the fetus and a placenta carried within the mother, said positioning occurring so as to allow detection of the umbilical blood flow information at an umbilical target location which is distal from a fetal umbilicus whereat the umbilical cord attaches to the fetus;

detecting umbilical blood flow information from the umbilical target location using the at least one umbilical flow detector;

deriving at least one umbilical flow measure from the umbilical blood flow information detected in said detecting step;

analyzing said at least one fetal heartbeat measure and said at least one umbilical flow measure to produce said at least one fetal health parameter.

29. A fetal monitoring system for monitoring a fetus carried within a mother, the system comprising:

at least one fetal heart sensor for sensing fetal heartbeat information;

at least one umbilical flow detector for detecting umbilical blood flow information which indicates flow of blood within an umbilical cord which extends between the fetus and a placenta carried by the mother;

at least one processor connected to receive said fetal heartbeat information from the at least one fetal heartbeat sensor, and connected to receive umbilical flow information from the at least one umbilical flow detector, said at least one processor deriving therefrom at least one fetal health parameter.

30. The system of claim 29 wherein said at least one fetal heartbeat sensor comprises at least one acoustical sensor.

31. The system of claim 29 wherein said at least one fetal heartbeat sensor comprises at least one ultrasonic heartbeat sensor subsystem.

32. The system of claim 29 wherein said at least one umbilical flow detector comprises an ultrasonic flowmeter.

33. The system of claim 29 wherein said at least one umbilical flow detector comprises a gated, pulsed-wave Doppler flowmeter.

34. The system of claim 29 wherein said at least one processor comprises a programmable microprocessor which is programmed to analyze said fetal heartbeat information and said umbilical flow information to determine said at least one fetal health parameter.

35. The system of claim 29 wherein said at least one fetal heartbeat sensor comprises at least one acoustical sensor; and said at least one umbilical flow detector comprises an ultrasonic flowmeter.

36. The system of claim 29 wherein:

said at least one fetal heartbeat sensor is an ultrasonic sensor which sensing fetal heart sounds;

said at least one umbilical flow sensor comprises a gated, pulsed-wave Doppler flowmeter;

said processor comprises a programmable microprocessor which is programmed to analyze said fetal heartbeat information and said umbilical flow information into said at least one fetal health parameter.

* * * * *